United States Patent [19]

Webinger

[11] 4,166,565
[45] Sep. 4, 1979

[54] AIR FRESHENER CARTON

[75] Inventor: George P. Webinger, Minneapolis, Minn.

[73] Assignee: Champion International Corporation, Stamford, Conn.

[21] Appl. No.: 913,904

[22] Filed: Jun. 8, 1978

[51] Int. Cl.² .......................... A61L 9/04; B65D 5/36
[52] U.S. Cl. ........................................ 229/8; 239/60; 229/37 R
[58] Field of Search ............................ 229/8, 4.5, 37; 239/51.5, 54, 55, 57, 60

[56] References Cited

U.S. PATENT DOCUMENTS

| | | | |
|---|---|---|---|
| 2,004,818 | 6/1935 | Luckett | 229/4.5 X |
| 2,050,894 | 8/1936 | Paige | 229/8 X |
| 2,067,998 | 1/1937 | Williamson | 229/8 X |
| 2,344,359 | 3/1944 | Lehmann | 229/4.5 X |
| 3,021,045 | 2/1962 | Morris | 229/8 X |
| 3,302,845 | 2/1967 | Gould | 229/8 X |
| 3,610,514 | 10/1971 | Samsing | 229/8 X |
| 3,821,423 | 6/1974 | Jamin | 229/8 X |
| 3,851,813 | 12/1974 | Smith | 229/4.5 X |
| 3,877,632 | 4/1975 | Steel | 229/8 |
| 3,910,495 | 10/1975 | Cummings et al. | 239/60 X |

FOREIGN PATENT DOCUMENTS 942748  11/1963  United Kingdom .......................... 229/8
1033661  6/1966  United Kingdom .......................... 229/8

Primary Examiner—Davis T. Moorhead
Attorney, Agent, or Firm—Evelyn M. Sommer

[57] ABSTRACT

A carton for holding an insert of air freshener material includes a front panel with outwardly bowed side edges and a spaced back panel having parallel upper and lower edges and converging side edges. First and second side panels connect the front and back panels. A top closure is formed of a plurality of flaps extending from the upper edges of the panels. The flaps extending from the front and back panels are sealed in overlapping fashion. The carton also includes a plurality of bottom flaps extending from the lower edges of the panels. The flaps extending from the front and back panels are also sealed in overlapping fashion.

10 Claims, 6 Drawing Figures

AIR FRESHENER CARTON

BACKGROUND OF THE INVENTION

The present invention relates to cartons and more particularly to a tapered carton having overlapping bottom panels.

Solid air freshers are sometimes sold in sealed outer cartons or containers having one or more openings in the container wall for allowing room air to circulate over the face of the solid material. The openings are covered with a panel of release paper or the like until a consumer is ready to use the air freshener. The release paper is then peeled from the face of the container to allow room air to begin circulating through the openings.

Molded plastic containers consisting of a molded shell and a separate, molded front piece have been employed to hold solid air freshener material. While known molded plastic containers have an aesthetically pleasing appearance, the costs of making and using such containers are higher than might be desired. The shell and front piece must be molded in separate operations and stored in unassembled form until the solid air freshener material is loaded into place. The front piece must then be glued or otherwise secured to the shell to provide a closed container.

The extra time required for the separate manufacturing operations and for the assembly operations can be translated into terms of increased manufacturing costs. The fact that the molded shells and front pieces must be stored in their molded form until they are to be used may create storage problems for the manufacturer.

SUMMARY OF THE INVENTION

The present invention is a low cost carton for holding an insert of solid air freshener material. The carton can be stored in a flattened or collapsed form until the solid material is loaded therein.

A carton constructed in accordance with the present invention may be fabricated from a one piece blank having a front panel with upper and lower edges defined by straight parallel fold lines and opposite ends defined by outwardly bowed fold lines. The blank would further include a back panel having upper and lower edges defined by straight parallel fold lines and opposite side edges defined by straight fold lines. A first side panel extends between one side edge of the front panel and one side edge of the back panel. A second side panel extends from the opposite side edge of the front panel. The blank has a plurality of top flaps including first and second side flaps extending from the fold lines at the upper edges of the first and second side panels, a back flap extending from the fold line at the upper edge of the back panel and a front flap extending from the upper edge of the front panel. The blank further includes a plurality of bottom flaps including first and second side flaps extending from the fold lines at the bottom edges of the first and second side panels, a back flap extending from the fold line at the lower edge of the back panel and a front flap extending from the fold line at the lower edge of the front panel.

A carton constructed in accordance with the present invention is erected from the described blank by securing the opposite free edges of the outermost panels. The top side flaps are folded inwardly, the top back flap is folded forward and the top front flap is folded backward into overlapping contact with the top back flap. An adhesive strip on a surface of one of these flaps secures the two flaps together. The bottom flaps are similarly secured with the bottom side flaps being folded inwardly first, the bottom back flap being folded forward and the bottom first flap being folded backward into overlapping contact with the back flap.

DESCRIPTION OF THE DRAWINGS

While the specification concludes with claims particularly pointing out and distinctly claiming that which is regarded as the present invention, further details of preferred embodiments of the invention may be more readily ascertained from the following detailed description when read in conjunction with the accompanying drawings wherein:

DETAILED DESCRIPTION

Figure 1:
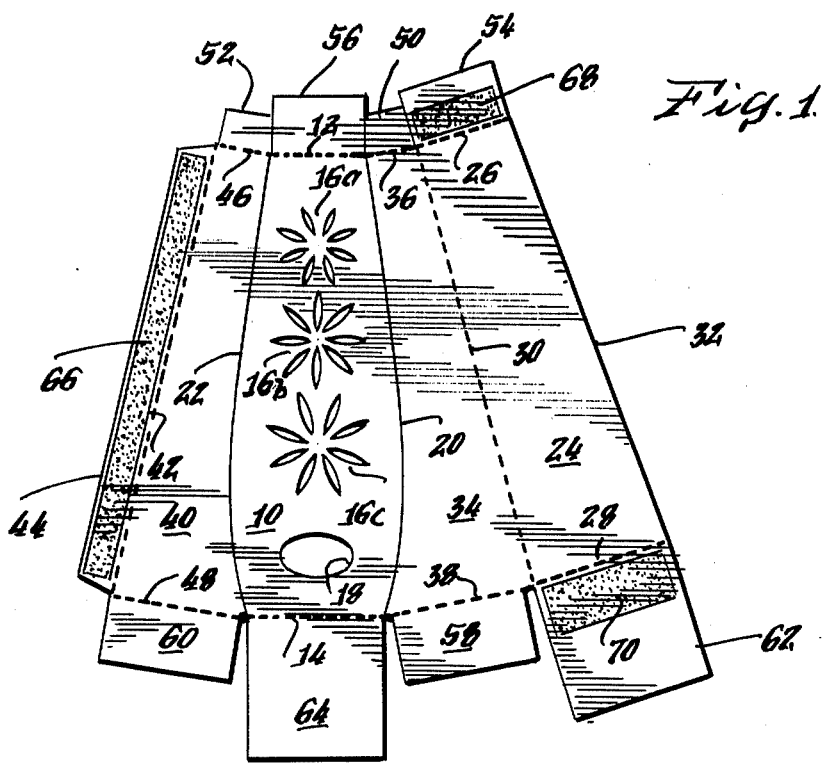
FIG. 1 is a plan view of a blank which may be used for manufacturing a preferred embodiment of the carton.

Referring now to FIG. 1, a blank suitable for manufacturing one embodiment of the invention is preferably formed from a single piece of foldable sheet material. A preferred type of sheet material is a paperboard material which is relatively inexpensive but which is relatively easily cut and scored. The blank includes a front panel 10 having an upper edge defined by a straight fold line 12 and a lower edge defined by another straight fold line 14. Front panel 10 includes one or more ornamental openings such as the three stylized flower cutouts 16a, 16b and 16c as well as an oval cutout 18. Where the carton is used as an air freshener material container, the cutouts permit room air to circulate into contact with the material. Opposite side edges of the front panel 10 are defined by outwardly bowed fold lines 20 and 22, respectively. It is also possible to use oval cutout 18 as a fill opening for introducing the air freshener material, i.e., the air freshener is admitted in a viscous but flowable form through cutout 18 and allowed to solidify within the carton.

The blank further includes a solid back panel 24 having an upper edge defined by a straight fold line 26 and a lower edge defined by another straight fold line 28. The right side edge 30 of the back panel 24 is defined by a straight fold line while the left edge 32 is preferably a straight, free edge. The edges 30 and 32 converge as they approach the upper edge 26 of the back panel 24. A first side panel 34 provides a solid web of material extending from the fold line 30 at the right edge of back panel 24 to the bowed fold line 20 at the left edge of front panel 10. The upper edge of the first side panel 34 is defined by a straight fold line 36 while the lower edge is defined by another straight fold line 38.

A second side panel 40 extends from the bowed fold line 22 at the right edge of front panel 10, terminating in a straight fold line 42 at the boundary between the second side panel 40 and an elongated glue flap 44. The upper edge of the second side panel 40 is defined by a fold line 46 while the lower edge is defined by another fold line 48.

The blank includes a plurality of top flaps including first and second top side flaps 50 and 52 extending upwardly from the fold lines 36 and 46 respectively. The top side flaps 50 and 52 have slightly tapered side edges. A top back flap 54 extends upwardly from the fold line 26 while a top front flap 56 extends upwardly from the fold line 12. Flaps 54 and 56 are substantially rectangular and have a length nearly equal to the length of the fold lines 36 and 46.

The blank further includes a plurality of bottom flaps including bottom side flaps 58 and 60 extending downwardly from the fold lines 38 and 48 of the side panels. A back bottom flap 62 extends downwardly from the fold line 28 while a front bottom flap 64 extends downwardly from fold line 14. The flaps 62 and 64 are substantially rectangular and have a length nearly equal to the width of the fold lines 38 and 48 at the lower edge of the side panels 34 and 40, respectively. The bottom flaps 58 and 60 are somewhat shorter and preferably include inwardly tapered side edges.

Selected surfaces of the blank are coated with an adhesive material which permits the blank to be easily erected into a closed, sealed carton. The surface of the glue flap 44 is coated with an adhesive strip 66 while the major portions of the surfaces of the top back flap 54 and the bottom back flap 62 are covered with adhesive layers 68 and 70, respectively.

A carton is made from the blank shown in FIG. 1 by folding the glue flap 44 into the plane of the paper or behind the front panel 10. The back panel 24 is then folded into the plane of the paper to bring the surface of the back panel 24 adjacent edge 32 into engagement with the adhesive strip 66, an irregularly-shaped, tapered tube exists. While this tube will not completely collapse, it is partially flattened and can be stored or shipped more readily than a fully erected tube.

Figure 2:
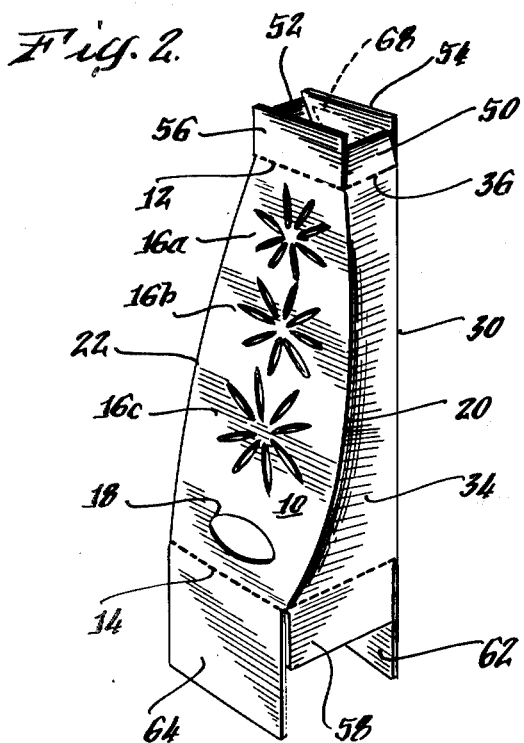
FIG. 2 is a perspective view showing the blank of FIG. 1 in partially erected form.

When the carton is to be put into use, the front and back panels and side panels are squared up as shown in FIG. 2. The top flaps and bottom flaps are still coplanar with the panels from which they extend. To seal the upper end of the carton, the top side flaps 50 and 52 are folded inwardly before the top back flap 54 is folded forward. When the flap 54 is folded forward, the adhesive coated area 68 is exposed to the interior of the carton. The final step in forming the top wall of the carton is to fold the top front flap 56 backward or into engagement with the adhesive-coated area 68. As indicated earlier, the length of the top front and back flaps 54 and 56 are substantially equal to the width of the fold lines 36 and 46 at the upper edges of the side panels 34 and 40.

Therefore, the front and back top panels overlap to provide a sealed, double-thickness top wall for the container.

Once an insert of a solid air freshener material is loaded into the container through the open bottom the bottom side flaps 58 and 60 are folded inwardly before the bottom back flap 62 is brought forward. When bottom back flap 62 is folded forward, the adhesive-coated area 70 is at the exterior of the container. Glue is also applied to the minor flaps 58 and 60 prior to closing flaps 62 and 64. This allows for a flat and stable bottom. Embossed feet may also be applied to panel 64 for greater stability. The final step in forming the bottom wall and completely sealing the container is to bring the bottom front flap 64 backward into contact with the adhesive-coated area 70. The front and back bottom flaps each are approximately as wide as the fold lines 38 and 48 at the lower edges of the side panels. Thus, the flaps 62 and 64 are overlapped at substantially the entire base area of the carton.

Figure 3:
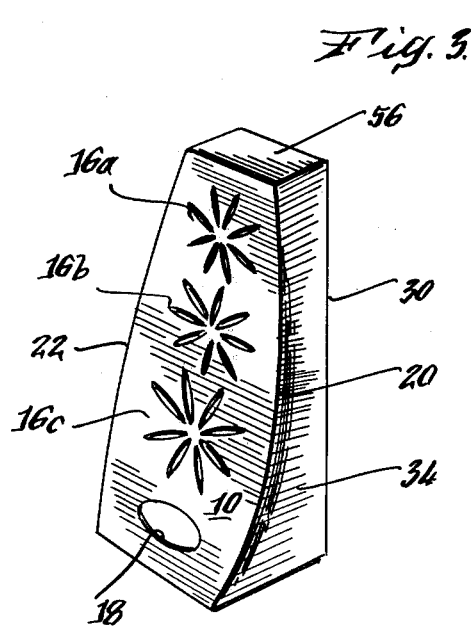
FIG. 3 is a perspective view showing a fully erected carton made from the blank of FIG. 1.

The fully erected carton is shown in perspective view in FIG. 3. Since the bottom wall or base of the carton is substantially larger than the top wall, the carton is extremely stable. Because the front and back flaps at both the top and the bottom of the carton overlap and are secured by relatively large areas of adhesive, the carton is quite durable.

While the blank and carton described with reference to the foregoing figures have shown the ornamental openings 16a, 16b, 16c and 18 in each view, it should be understood that the entire front panel 10 will probably be covered by an impervious sheet of release paper at a point in the manufacturing process prior to the time the solid air freshener material is loaded into the carton. This layer of release paper will remain in place until removed by the consumer to permit air to circulate through the openings in the front panel.

Figure 5:
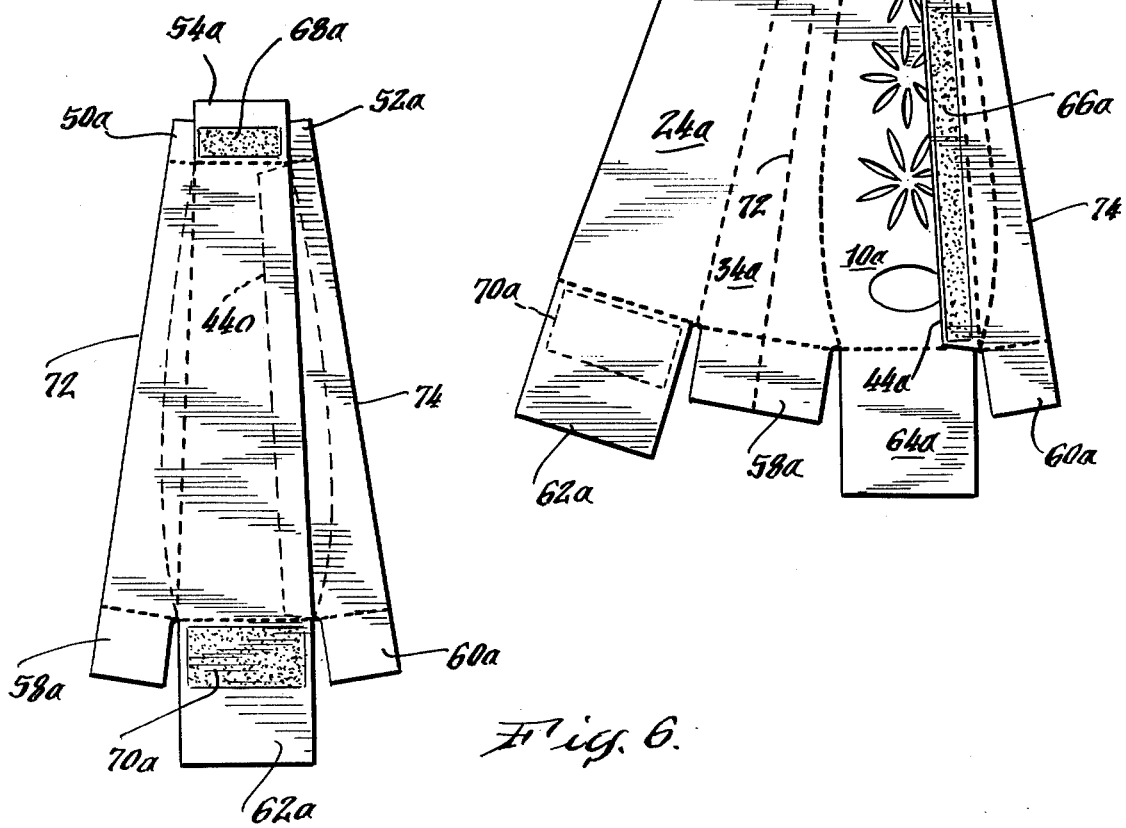
FIG. 5 is a plan view of the blank of FIG. 4 during one step in the fabrication of the carton.
Figure 6:
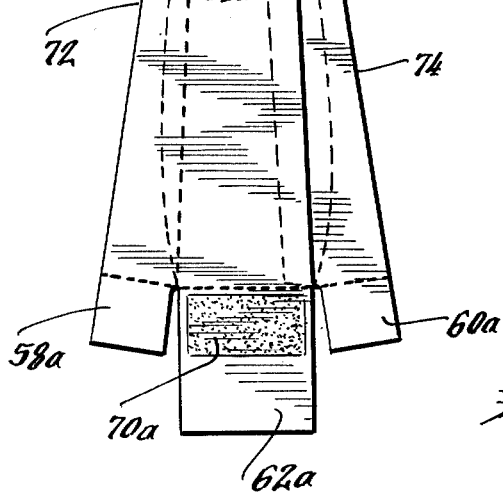
FIG. 6 is a plan view of the blank of FIG. 4 during a subsequent step in the fabrication of the carton.

Another preferred embodiment of the invention is described with reference to FIGS. 4–6. The blank from which the second embodiment is fabricated is very similar to the blank described with reference to FIG. 1. Most of the corresponding components of the two blanks are identical. For example, the blank shown in FIG. 4 includes a front panel 10a, a back panel 24a, and first and second side panels 34a and 40a. The blank further includes top side flaps 50a and 52a, a top front flap 56a and a top back flap 54a. Further, the blank includes bottom side flaps 58a and 60a, a bottom front flap 64a and a bottom back flap 62a. Finally, the blank includes a trapezoidal glue flap 44a.

Figure 4:
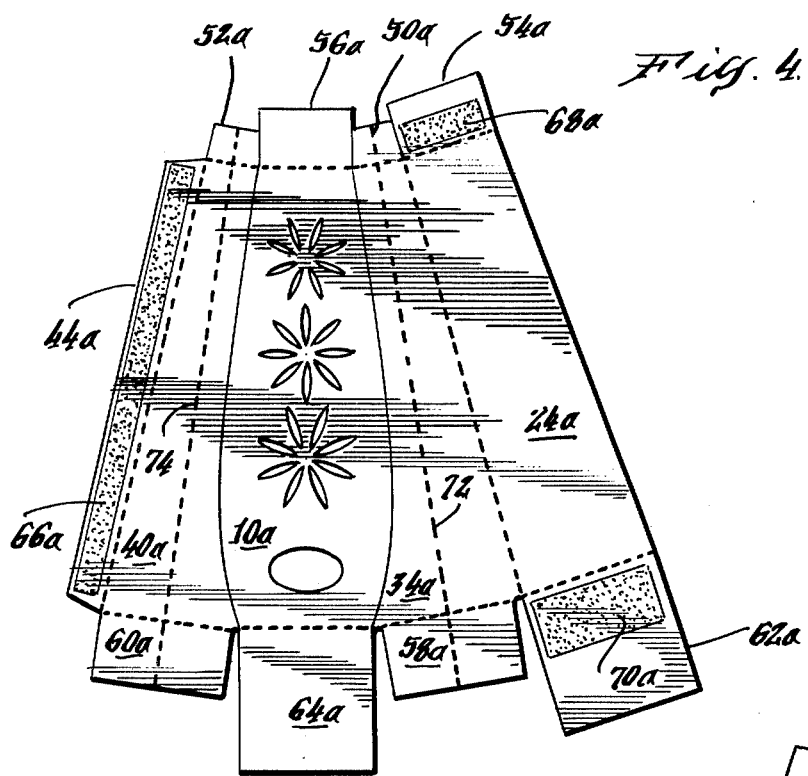
FIG. 4 is a plan view of an alternate embodiment of a blank for manufacturing a carton in accordance with the present invention.

The only difference between the blanks shown in FIGS. 1 and 4 is that the side panels 34 and 40 of the blank shown in FIG. 1 are unscored. The side panels 34a and 40a of the blank shown in FIG. 4 are bisected by straight fold lines 72 and 74, respectively. The fold lines extend approximately from the midpoint of each outer edge of bottom side flap to the midpoint of the outer edge of each top side flap.

To erect a carton from the blank shown in FIG. 4, the blank is first placed face down and the glue flap 44a and one half of side panel 40a folded as a unit about the fold line 74 so that glue flap 44a overlies a portion of the front panel 10a. When this fold is made, the adhesive strip 66a will be in view. The back panel 24a and one half of the side panel 34a are then folded as a unit about the fold line 72 to bring the left edge of back panel 24a into registry with the glue flap 44a. The carton is in a completely collapsed condition after this fold is made but can be easily erected in the same manner as the first described embodiment without the need for additional gluing steps.

The extra score lines thus not only make it easier to manually form the initial tapered tube but also permit the carton to be stored in a completely collapsed or flattened condition until it is needed.

While there have been described what are considered to be preferred embodiments of the invention, variations and modifications therein will occur to those skilled in the art once they become acquainted with the basic concepts of the invention. Therefore, it is intended that the appended claims shall be construed to include all such variations and modifications as fall within the true spirit and scope of the invention.

What is claimed is:

1. A tapered carton made from a blank of foldable sheet material for holding an insert of air freshener material comprising:
   a front panel having parallel upper and lower edges and opposite outwardly bowed side edges;
   a back panel having parallel upper and lower edges and tapered side edges;
   a first side panel connecting one side edge of said front panel to one side edge of said back panel;
   a second side panel connecting the other side edge of said front panel to the other side edge of said back panel;
   a top closure comprising first and second top side flaps extending from the upper edges of said first and second side panels, a top back flap extending from the upper edge of said back panel and a top front flap extending from the upper edge of said front flap, said top back flap and said top front flap overlapping one another;
   a bottom closure comprising first and second bottom side flaps extending from the lower edges of said first and second side panels, a bottom back flap extending from the lower edge of said back panel, a bottom front flap extending from the lower edge of said front panel, said bottom back flap and said bottom front flap being substantially coextensive and being secured to one another in overlapping manner;
   said bottom closure having a larger exposed surface then said top closure to form a stable base for said carton.

2. A tapered carton as defined in claim 1 wherein said front panel includes ornamental openings for exposing material held within the carton.

3. A tapered carton as defined in claim 2 wherein said first and second side panels include score lines extending between their upper and lower edges.

4. A tapered carton as defined in claim 3 wherein each of said score lines extend along a straight line from the midpoint of the lower edge to the midpoint of the upper edge of the side panel.

5. A tapered carton as defined in either of claims 2 and 4 further including a glue flap connected to the free side edge of said second side panel, said glue flap having an adhesive coating on one surface for engagement with the inner surface of said back panel.

6. A one-piece blank for a tapered carton adapted to receive an insert of air freshener material comprising:
   a front panel having upper and lower edges defined by straight parallel fold lines and opposite side edges defined by outwardly bowed fold lines;
   a back panel having upper and lower edges defined by straight parallel fold lines and opposite side edges defined by straight fold lines;
   a first side panel extending between one side edge of said front panel and one side edge of said back panel, the lower edge of said first side panel being longer than the upper edge;
   a second side panel extending from the other side edge of said front panel, the lower edge of said second side panel being longer than the upper edge;
   a plurality of top flaps comprising first and second side flaps extending upwardly from the fold lines defining the upper edges of said first and second side panels, a back flap extending from the fold line defining the upper edge of said back panel and a front flap extending from the fold line defining the upper edge of said front panel; and
   a plurality of bottom flaps comprising first and second side flaps extending downwardly from the fold lines defining the lower edges of said first and second side panels, a back flap extending downwardly from the fold line defining the lower edge of said front panel,
   said front and back bottom flaps being significantly larger than said front and back top flaps.

7. A one piece blank for a tapered carton as defined in claim 6 wherein said front panel includes ornamental openings.

8. A one piece blank for a tapered carton as defined in claim 7 wherein said front and back bottom panels are substantially the same size.

9. A one piece blank for a tapered carton as defined in claim 8 wherein the length of said front bottom panel is substantially equal to the length of the lower edge of one of said side panels.

10. A one piece blank for a tapered carton as defined in claim 9 wherein each of said first and second side panels is bisected by a score line extending between the midpoint of the upper edge and the midpoint of the lower edge of the side panel.

* * * * *